(12) United States Patent
Crane et al.

(10) Patent No.: US 9,292,475 B1
(45) Date of Patent: Mar. 22, 2016

(54) METHOD AND SYSTEM FOR PROCESSING INFORMATION

(71) Applicant: Glooko Inc., Palo Alto, CA (US)

(72) Inventors: Ronald C. Crane, Mountain View, CA (US); Evan A. Green, Portola Valley, CA (US); Daniel S. Sherbeck, Los Altos Hills, CA (US); Michael Ortiz, San Francisco, CA (US)

(73) Assignee: Glooko Inc., Palo Alto, CA (US)

( * ) Notice: Subject to any disclaimer, the term of this patent is extended or adjusted under 35 U.S.C. 154(b) by 254 days.

(21) Appl. No.: 14/140,271

(22) Filed: Dec. 24, 2013

(51) Int. Cl.
*G06F 17/10* (2006.01)

(52) U.S. Cl.
CPC ........................... *G06F 17/10* (2013.01)

(58) Field of Classification Search
None
See application file for complete search history.

(56) References Cited

U.S. PATENT DOCUMENTS

| | | | | |
|---|---|---|---|---|
| 6,812,824 | B1* | 11/2004 | Goldinger | G06K 17/00 340/10.1 |
| 2003/0099180 | A1* | 5/2003 | Park | G11B 7/0053 369/59.25 |
| 2006/0251114 | A1 | 11/2006 | Nuggehalli et al. | |
| 2007/0064776 | A1* | 3/2007 | Feller | H04B 1/7085 375/149 |
| 2007/0069784 | A1* | 3/2007 | Shin | H03K 17/163 327/170 |
| 2007/0231209 | A1 | 10/2007 | Cosentino et al. | |
| 2007/0299318 | A1 | 12/2007 | Chen et al. | |
| 2008/0097908 | A1 | 4/2008 | Dicks et al. | |
| 2008/0181289 | A1* | 7/2008 | Moll | H04L 1/242 375/224 |
| 2008/0281840 | A1 | 11/2008 | Fennell et al. | |
| 2009/0112626 | A1 | 4/2009 | Talbot et al. | |
| 2009/0296742 | A1 | 12/2009 | Sicurello et al. | |
| 2010/0094098 | A1 | 4/2010 | Smith et al. | |
| 2013/0212168 | A1 | 8/2013 | Bonasera et al. | |

OTHER PUBLICATIONS

Dalal et al., "Method and System for Monitoring a Medical Condition," U.S. Appl. No. 14/014,179, filed Aug. 29, 2013.

* cited by examiner

*Primary Examiner* — David H Malzahn
(74) *Attorney, Agent, or Firm* — Hawley Troxell Ennis & Hawley LLP; Sean P. Lewis; Philip McKay (57) ABSTRACT

A method and apparatus for processing information includes receiving electronic information at a second device from a first device, where the received electronic information is sampled periodically, resulting in a plurality of numerical data value samples. The data value samples are analyzed within the receiver to determine slope transitions within the data which are interpreted as high and low transitions representative of bit transitions ordinarily seen in the transmission of digital data. The bit transitions are then converted into a receiving device appropriate usable and readable form, such as bytes (8 bits each) or groups of bytes, as needed. Data bytes may be commands, information, or other indicators useful to the receiving device.

20 Claims, 6 Drawing Sheets

METHOD AND SYSTEM FOR PROCESSING INFORMATION

BACKGROUND

Modern electronic systems often include two or more system components that share information in order to accomplish one or more tasks. Information is often required to be transmitted by one device and received by another, in order for the second device to use the transmitted information. A high degree of accuracy in the interpretation of the information at the receiver is desired in order to ensure high confidence in the result of operations performed on the interpreted information.

System components and methods for exchanging data between a transmitter and a receiver often involve very stable receiving baselines, and protocols and processes used to interpret information being received by the stable components depend on the low variability in the receiver to accurately interpret the incoming information. Design considerations for such very stable systems need not include consideration regarding changing conditions within the receiver.

When receiving information via standard audio circuitry, it is not uncommon for baselines to vary widely during a given information transmission period. Systems and methods that rely on stable baselines and amplitudes are ineffective in these situations.

SUMMARY

In accordance with one embodiment, a method and system for processing information includes receiving electronic information at a second device from a first device, where the received electronic information is sampled periodically, resulting in a plurality of numerical data value samples. The data value samples are analyzed within the receiver to determine slope transitions within the data which are interpreted as high and low transitions representative of bit transitions ordinarily seen in the transmission of digital data. The bit transitions are then converted into a receiving device appropriate usable and readable form, such as bytes (8 bits each) or groups of bytes, as needed. Data bytes may be commands, information, or other indicators useful to the receiving device.

In one embodiment, the data value samples represent successive periodic samples taken of an incoming signal being provided to the second device by the first device. In one embodiment, sampling is performed at sampling events, with each sampling event separated by a sampling period.

In one embodiment, analysis of the data value samples is performed to determine a first point where an absolute value of the slope of the data first exceeds a predetermined slope threshold.

In one embodiment, analysis of the data value samples is performed to determine a second point, later in time than the first point, where an absolute value of a computed slope of the data is first below the predetermined slope threshold.

In one embodiment, analysis of the data value samples is performed to determine a third point, later in time than the second point, where an absolute value of a slope of the data value samples first exceeds the predetermined slope threshold.

In one embodiment, analysis of the data value samples is performed to determine a fourth point later in time than the third point, where an absolute value of a slope of data value samples falls below the predetermined slope threshold.

In one embodiment a determination is made of a number of bits of information that have been received between the previously determined first and fourth points. In one embodiment, the number of bits is determined through identifying how many sampling periods have occurred between a first midpoint of a first line and a second midpoint of a second line, where the first line is represented by using the first and second points as endpoints and the second line being represented by using the third and fourth points as endpoints.

In one embodiment, a determination is made that the bits of information that have been identified are high bits representing a binary high. In one embodiment, the determination that the identified bits are high bits is made by determining that the slope at the first point is positive.

In one embodiment, a determination is made that the bits of information that have been identified are low bits representing a binary low. In one embodiment, the determination that the identified bits are low bits is made by determining that the slope at the first point is negative.

In one embodiment, a determination is made of how many sampling periods have occurred between the first point and the third point and comparing a time represented by the determined number of sampling periods to an expected frequency of the received electronic information.

In one embodiment, a determination is made of how many sampling periods have occurred between the second point and the fourth point and comparing a time represented by the determined number of sampling periods to an expected frequency of the received electronic information.

In one embodiment, a determination is made of a number of sampling periods following the determination of any of either the first point, the second point, the third point, or the fourth point exceeds a predetermined slope degradation threshold and, in response, reducing the slope threshold by a previously determined amount.

BRIEF DESCRIPTION OF THE DRAWINGS

Common reference numerals are used throughout the drawing figures and the detailed description to indicate like elements. One skilled in the art will readily recognize that the above drawing figures are examples and that other architectures, modes of operation, orders of operation and elements/functions can be provided and implemented without departing from the features of the invention, as set forth in the claims.

DETAILED DESCRIPTION

Embodiments will now be discussed with reference to the accompanying drawings, which depict one or more exemplary embodiments. Embodiments may be embodied in many different forms and should not be construed as limited to the embodiments set forth herein, shown in the drawings, and/or described below. Rather, these exemplary embodiments are provided to allow a disclosure of the principles of the invention, as set forth in the claims, to those of skill in the art.

As used herein, the term "computing system", and the term "application platform" includes, but is not limited to, a desktop computing system; a portable computing system; a mobile computing system; a laptop computing system; a notebook computing system; a tablet computing system; a workstation; a server computing system; a mobile phone; a smart phone; a wireless telephone; a two-way pager; a Personal Digital Assistant (PDA); a media player, i.e., an MP3 player and/or other music and/or video player; an Internet appliance; or any device that includes components that can execute all, or part, of any one of the processes and/or operations as described herein. In addition, as used herein, the term computing system, can denote, but is not limited to, systems made up of multiple desktop computing systems; portable computing systems; mobile computing systems; laptop computing systems; notebook computing systems; tablet computing systems; workstations; server computing systems; smart phones; wireless telephones; two-way pagers; Personal Digital Assistants (PDAs); media players; Internet appliances; or any devices that can be used to perform the processes and/or operations as described herein.

As used herein, the term "network" includes, but is not limited to, any network or network system such as, but not limited to, a peer-to-peer network, a hybrid peer-to-peer network, a Local Area Network (LAN), a Wide Area Network (WAN), a public network, such as the Internet, a private network, a cellular network, a POTS network; any general network, communications network, or general network/communications network system; a wireless network; a wired network; a wireless and wired combination network; a satellite network; a cable network; any combination of different network types; or any other system capable of allowing communication between two or more computing systems, whether available or known at the time of filing or as later developed.

In one embodiment, a process for processing information includes one or more applications, such as software packages, modules, or systems, implemented on one or more computing systems.

In accordance with one embodiment, a method and system for transforming data includes receiving electronic information at a second device from a first device, where the received electronic information includes a plurality of numerical data value samples.

On one embodiment, the first device and the second device are coupled through a network.

In one embodiment, the first device is any device that has information needed by the second device for any reason. In one embodiment, the first device is a data gathering device or a measurement device and the second device is a smartphone. Other devices suitable for the practice of the process operations described herein may be employed by those of ordinary skill having the benefit of this disclosure.

In one embodiment, the first device is a measurement device such as a medical device measuring the status of a medical condition. Such medical devices may include a blood glucose meter, a blood pressure meter, an oximeter, or any measurement device known to persons of ordinary skill, or any such device later developed. Though medical devices have been presented herein as examples of devices that may be employed in a system utilizing the process operations disclosed herein, persons of ordinary skill will readily recognize that any system having a first device that transmits information to any second device may employ the process operations disclosed herein, when appropriate.

In one embodiment, the data value samples described above represent successive periodic samples taken of an incoming signal being provided to the second device by the first device. In one embodiment, sampling is performed at sampling events, with each sampling event separated by a sampling period.

In one embodiment, analysis of the data value samples taken at sampling events is performed to determine a first point which is a data value sample selected from a set of data value samples used to determine a slope, where an absolute value of the slope of the data first exceeds a predetermined slope threshold. Any of the data value samples of the set of data value samples may be selected as the first point. In one embodiment, using a set of two data value samples to determine a slope, a first data value sample is selected as the first point, assuming other criteria for establishing the first point is satisfied.

In one embodiment, using a set of two data value samples to determine a slope, the second data value sample is selected as the first point, assuming other criteria for establishing the first point is satisfied.

In one embodiment, using first and third data values of a set of three data value samples to determine a slope, a first data value sample is selected as the first point.

In one embodiment, using first and third data values of a set of three data value samples to determine a slope, the third data value sample is selected as the first point, assuming other criteria for establishing the first point is satisfied.

Correspondingly, when operations are performed to determine a second point, a third point, and a fourth point, any of the data value samples of the set of data value samples used to determine the appropriate slope may be selected as those points as well.

Embodiments are contemplated where two, three, or more than three sampling periods are used for this determination and/or one or more of the determinations of second, third, and fourth points described later, depending on the particular application and system employing the process.

In various embodiments, slopes are determined for each pair, triple, or any other set of data value samples desired by a designer. Each determined slope may be recorded and/or stored for later use, or alternatively used in live analyses, or both, depending on constraints and design parameters associated with an application employing the invention.

Embodiments listed herein may be employed separately, or combined as needed, depending on constraints and design parameters associated with an application, system, or process employing the invention.

In one embodiment, analysis of the data value samples is performed to determine a second point, later in time than the first point, where an absolute value of the slope of the data is first below the predetermined slope threshold.

In one embodiment, analysis of the data value samples is performed to determine a third point, later in time than the second point, where an absolute value of a slope of the data value samples first exceeds the predetermined slope threshold.

In one embodiment, analysis of the data value samples is performed to determine a fourth point later in time than the third point, where an absolute value of a slope of data value samples falls below the predetermined slope threshold.

In one embodiment, a determination is made of a number of bits of information that have been received between the previously determined first and fourth points. In one embodiment, the number of bits is determined through identifying how many sampling periods have occurred between a first midpoint of a first line and a second midpoint of a second line, where the first line is represented by using the first and second points as endpoints and the second line being represented by using the third and fourth points as endpoints.

In one embodiment, a determination is made that the bits of information that have been identified are high bits representing a binary high. In one embodiment, the determination that the identified bits are high bits is made by determining that the slope at the first point is positive.

In one embodiment, a determination is made that the bits of information that have been identified are low bits representing a binary low. In one embodiment, the determination that the identified bits are low bits is made by determining that the slope at the first point is negative.

In one embodiment, a determination is made of how many sampling periods have occurred between the first point and the third point and comparing a time represented by the determined number of sampling periods to an expected frequency of the received electronic information. Processing may be accomplished and bit transitions determined, each time a transition occurs, in groups of high bit and groups of low bits, or in groups of high and low bits scattered throughout data collected over 10, 50, 100, or a different number of sampling periods, as desired according to the application employing the process.

In one embodiment, a determination is made of how many sampling periods have occurred between the second point and the fourth point and comparing a time represented by the determined number of sampling periods to an expected frequency of the received electronic information.

In one embodiment, at any time during processing, there may be a number of consecutive sampling periods over which various slopes of the data are determined as described herein. A count may be kept of how many slopes in a row where the absolute values of those slopes fail to exceed the slope threshold. At a time when the count exceeds a predetermined slope degradation threshold, the slope threshold may be reduced by a predetermined amount or predetermined percentage, and the count reset to zero.

Processing of received information may be accomplished and bit transitions determined, each time a transition occurs, in groups of high bits and groups of low bits, or in groups of high and low bits scattered throughout data collected over 10, 50, 100, or a different number of sampling periods, as desired according to the application employing the process.

Figure 1:
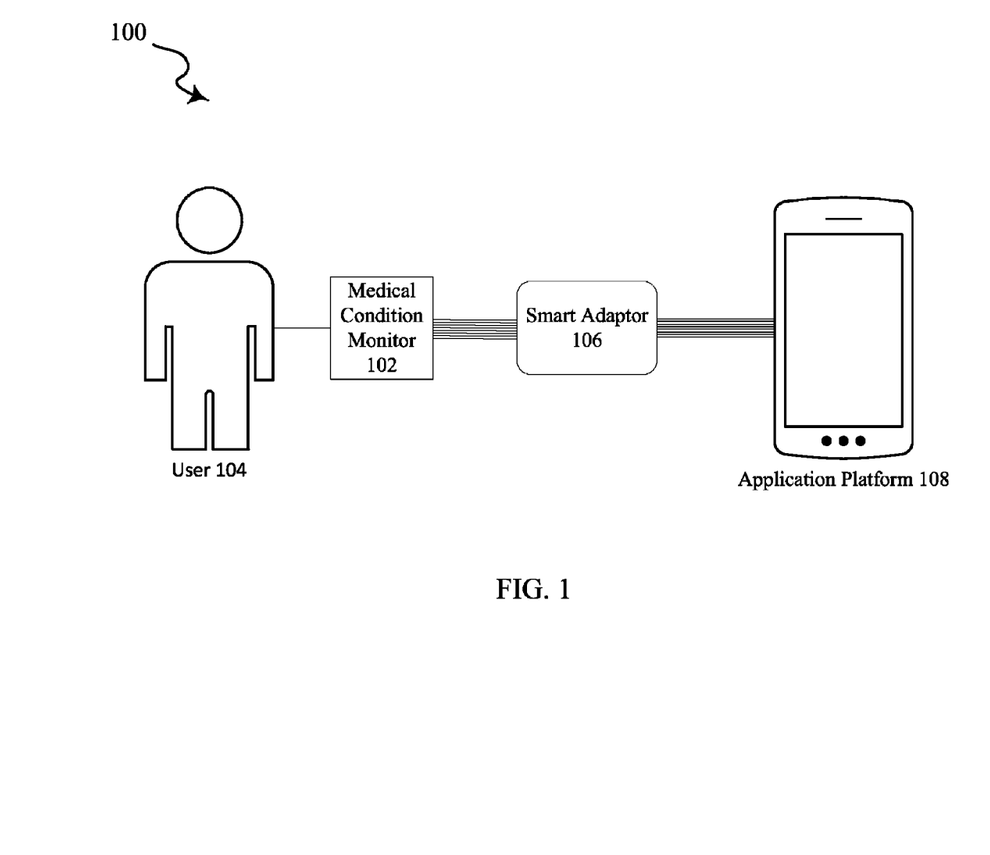
FIG. 1 is a system diagram of an exemplary architecture for one embodiment of a system for transforming data.

FIG. 1 is a system diagram of an exemplary architecture for one embodiment of a system for monitoring a medical condition. Similarities may be seen between the system of FIG. 1 and the system depicted in application Ser. No. 14/014,179 filed Aug. 29, 2013 titled METHOD AND SYSTEM FOR MONITORING A MEDICAL CONDITION which is incorporated herein by reference in its entirety.

In the embodiment of FIG. 1, System 100 includes a Medical Condition Monitor 102 configured to determine a status of a medical condition associated with a user, for example, User 104. Medical Condition Monitor 102 is exemplary of a typical device which may be used as a first device. As described herein, many other devices are also contemplated and may be used to transmit data to a second device employing the process operations described herein.

System 100 further includes Application Platform 108 which is coupled to Medical Condition Monitor 102 through Smart Adaptor 106. Smart Adaptor 106 is optional. In one embodiment, Medical Condition Monitor 102 is coupled to Application Platform 108 without utilizing Smart Adaptor 106.

Herein, an "Application Platform" includes, but is not limited to: a smart phone, a cellular phone, a digital wireless telephone, a tablet computing system, a notebook computing system, any portable computing system, a two-way pager, a Personal Digital Assistant (PDA), a media player, i.e., an MP3 player and/or other music and/or video player, a server computer, an Internet appliance, or any other device and/or computing system that includes components that can execute all, or part, of any one of the processes and/or operations as described herein.

In one embodiment, Application Platform 108 may be coupled to Medical Condition Monitor 102 through a network, such as, but not limited to, any general network, communications network, or general network/communications network system, a cellular network, a wireless network, a combination of different network types, or other wireless, wired, and/or a wireless and wired combination network, a public network, a private network, a satellite network, a cable network, or any other network capable of allowing communication between two or more systems or system components, as discussed herein, and/or available or known at the time of filing, and/or as developed after the time of filing.

Typically, Application Platform 108, a second device, is coupled to Medical Condition Monitor 102, a first device, through an analog port of Application Platform 108. One example of an analog port that might be available if Application Platform 108 is a smartphone, for example, is an audio port suitable for receiving and transmitting audio information.

Examples of medical condition monitors include, but are not limited to blood glucose monitors (including continuous glucose monitors), insulin pumps, and oximeters. Other medical condition monitors may further include, but are not limited to, lifestyle devices such as weight measurement devices, body fat measurement devices, exercise equipment, blood pressure measurement devices, heart rate measurement devices, and other medical condition monitors known to those of ordinary skill or which are later developed. Although a medical condition monitor such as Medical Condition Monitor 102 has been used herein as an exemplary first device from which Application Platform 108 may receive data, many other devices are also contemplated for use with the process operations described herein. Any device having an analog data output may be used as a first device from which the second device, e.g. Application Platform 108 receives data.

Application Platform 108 may include typical components known to those of ordinary skill in the art, including, but not limited to a central processing unit (CPU), an input/output (I/O) interface, and a memory system, including cache memory. In one embodiment, a memory system of Application Platform 108 includes all, or part, of a process for processing information, described below. Instructions to perform one or more of the process operations described herein may alternatively and optionally be embedded and executed by a hardware component such as an Application Specific Integrated Circuit (ASIC), a programmable logic array, or any other component suitable for performing the process operations.

Figure 2:
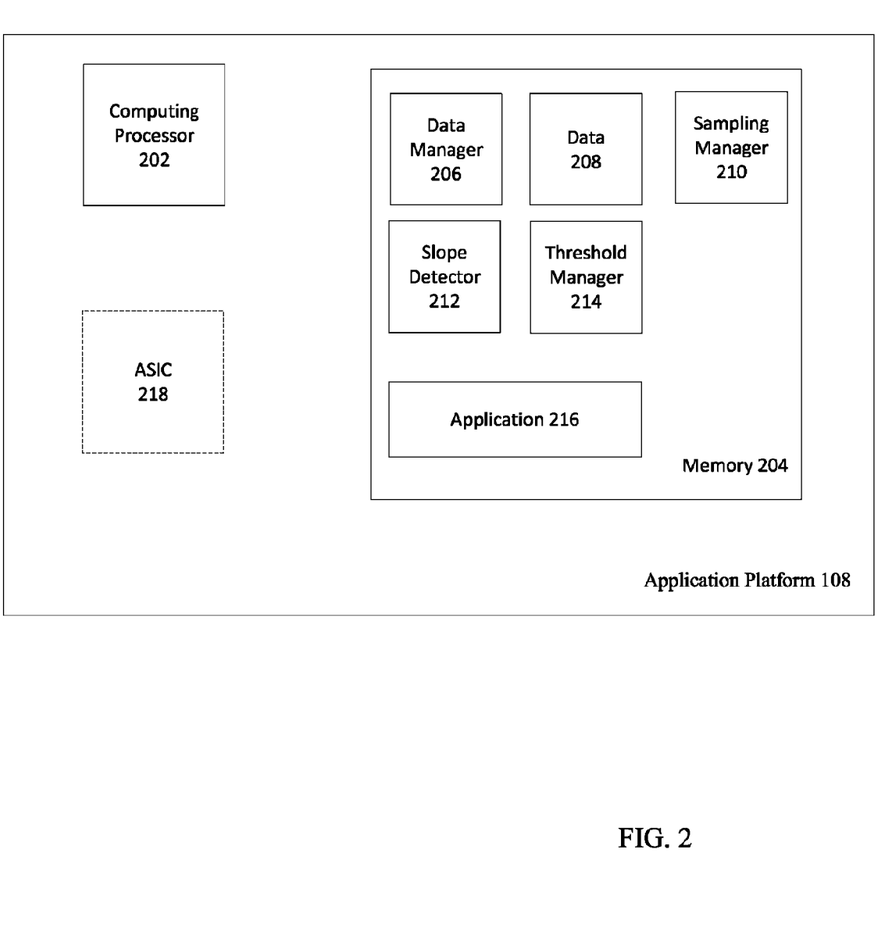
FIG. 2 is a block diagram depicting an application platform in accordance with one embodiment.

FIG. 2 is a block diagram depicting an application platform in accordance with one embodiment.

Referring to FIG. 2, Application Platform 108 includes Computing Processor 202 and Memory 204 coupled to Computing Processor 202. Although one computing processor, such as Computing Processor 202, and one memory, such as Memory 204 are shown, the process may optionally be spread across two or more computing processors or two or more memories, or a combination of two or more computing processors and two or more memories. Processor executable instructions are stored within Memory 204 which, when executed by Computing Processor 202 perform the process operations described herein.

More particularly, Memory 204 includes instructions configured to operate as Data Manager 206 which manages Data 208, Sampling Manager 210 which manages data value samples, Slope Detector 212 which determines a slope of the data value samples according to criteria discussed herein, and Threshold Manager 214 which makes determinations regarding a slope degradation threshold described below and also manages the real-time determination of the slope thresholds.

Also included within Memory 204 is Application 216 which is a destination for the information being received from the first device, such as Medical Condition Monitor 102 of FIG. 1.

In one embodiment, an application, process, or program is defined to include executable code. Moreover, those of skill in the art will understand that when it is said that an application, process, or an operation takes some action, the action is the result of executing one or more instructions by a computing processor.

In various embodiments, prior to the beginning of data sampling, test samples may be obtained to determine a degree of noise activity that is statically present in Application Platform 108. As an illustrative example, data value samples taken prior to any information being sent from the first device might result in six data value samples: 10, 0, 10, 5, 8, 7. In one embodiment, following the sixth data value sample of 7, information from the first device is received at the second device, with the first "real" information resulting in a data value sample of 30. In various embodiments, an atypical noise value being received, such as a data value at least three times the value of an immediately prior data value, here seen in this example as an immediate prior data value sample of 7, is seen as the beginning of actual data to be used for determining a slope, for example, and is treated as such by the process for processing information as discussed herein.

In one or more embodiments, data is expected to be received in a particular format, with one or more bits particularly designated, such as the first or last bit in a given string of bits being a high bit representing a binary one "1", or the first or last bit in a given string of bits being low bit representing a binary zero "0". Other groupings for leading and trailing bits including a "10", "01", "11" and "00" constructs, or with three or more bits in a similar fashion, depending on the design of the system.

In various embodiments, the sampling rate is a multiple of the expected frequency of the data transmission from the first device. For example, an expected data frequency might be 9600 bits per second, or more or less, with a sampling rate of approximately 44,100 samples per second, or more, or less. Other data sampling rates and other expected data transmission frequencies may be used along these guidelines while remaining within the scope and purpose of the process for processing information disclosed herein.

Further, in various embodiments, a slope of earlier incoming data values is obtained prior to designating the incoming data that follows as valid, to ensure that the received data value sample represent actual data. In various embodiments, the obtained slope is an absolute value of the difference of two data value samples, divided by the number of data sampling periods over which the data value samples were obtained.

In one embodiment, an average slope may be used in place of other slope determining methods at one or more process operations where a slope is determined, using three or more data value samples taken over two or more data sampling periods. In one example, three data value samples are used, and an average slope is determined by averaging a first slope with a second slope, with the first slope being determined from a first data value sample and a second data value sample, and the second slope being determined from the second data value sample and a third data value sample. More than three data samples may be used to determine an average slope, consistent with this disclosure.

In one illustrative example of a slope determination, in an obtained data value sample set having data value samples 10, 29, and 85, two data sampling periods are involved, the first data sampling period being between the time the first data sample of 10 was obtained and the second data sample value of 29 was obtained, and the second data sampling period being between the time the second data sample of 29 was obtained and the third data sample value of 85 was obtained.

In this illustrative example, and in one embodiment, the first two exemplary data samples are used to calculate a slope, the difference between the first two data value samples is obtained, resulting in 19, and is subsequently divided by the number of sampling periods between the two data points, e.g. one, resulting in a slope of 29 minus 10 equals 19.

This particular calculation of slope uses $$\text{slope} = \frac{|y_n - y_1|}{n-1}$$

where the values of y are the later and earlier data value samples being considered, respectively, and the difference calculation in the denominator is merely the number of sampling periods between the values used in the numerator. Thus, if the data value samples are 10 and 29, the numerator is 19 (the second data value samples minus the first) and the denominator is 1, the number of sample periods between the two data value samples used in the numerator.

In a second illustrative example using the same data samples from above, and in one embodiment, the first and third exemplary data samples are used to calculate a slope, the difference between the two data value samples is obtained, resulting in 85 minus 10 equaling 75, and is subsequently divided by the number of sampling periods between the two data points, e.g. two, in this example, resulting in a slope of 75 divided by two equaling 37.5.

In one embodiment, initial edge detection is accomplished by determining a sample event where the slope of the data value samples near that event are equal to or more than a predetermined multiple of the prior slopes. In one illustrative example, a multiple of 3 is set as a threshold. Thus, on initial detection of what is believed to be data incoming from the first device, if the slope of a proposed initial edge is at least three times a prior slope of the data values samples preceding it, it is believed that an initial edge has been detected.

Alternatively, in another illustrative example, and in one embodiment, in order to validate a particular sampling event as being part of a true initial edge, as compared with being a noise spike, an increase in an absolute value of a slope greater than a predetermined threshold is desired. In one illustrative example, the desired difference in slope is 20. Thus, in order to validate a slope for initial edge detection, an absolute value of a second slope would have to exceed an absolute value of an immediately prior slope by the threshold amount. In one embodiment, the initial edge detection slope is 20. Thus, in this illustrative example, an initial edge would be considered to be detected if the absolute value of a first slope is 20 units less than an absolute value of the slope that successively follows the first.

In a prior example, a first calculated slope was 19 and a second calculated slope was 37.5. Since 37.5 is not greater than 19 by more than 20, that second slope would not be considered to be part of an initial edge.

Using the process described above, rising and falling edges may be detected. In one embodiment, for slopes that are not part of an initial edge, a slope threshold may be used to determine a rising or falling "edge" in the data.

Once the slope magnitude is greater than or equal to the slope threshold, the process detects that the beginning of an edge has been found.

The process continues to record data value samples and notice is taken when the constantly computed slope magnitude falls below the slope threshold. Once the current slope magnitude has fallen below the slope threshold, the edge is determined to have just passed. One of the data value samples used to determine that current slope magnitude is determined to be the edge end point, and therefore the end of the edge.

The edge center point may then be found by finding the largest magnitude slope between the edge start point and the edge end point and subtracting ([samples per slope]−1)/2. For example, in one illustrative example where the number of samples being used to compute each slope is 3, then the time coordinate of the edge center point is the coordinate of the largest magnitude slope minus [(3−1)/2]=2/2=1.

This is also formulated as $$\text{edge midpoint} = x \text{ coordinate} - \frac{(\text{samples per slope} - 1)}{2},$$

where the x coordinate terminates the segment with the largest slope.

In various embodiments, once an edge is found using the process operations described above, a slope threshold is set such that the absolute value of future slopes above that threshold may be considered to be a part of subsequent edges. Initially and illustratively, in one embodiment, the initial slope threshold is set to a fraction of the absolute value of the slope found when determining the initial edge. In one example, the slope threshold is set to 9/16ths of the absolute value of the slope of the initial edge. Thus, in one illustrative example, if the initially detected edge has a slope of 64, the slope threshold is set, in this illustrative example, to 64×(9/16)=36. In various embodiments, a new slope threshold is dynamically recalculated after each edge has passed.

Due to variations within a receiving device, baselines may change significantly over a long period of time involving many data sampling periods. In order to compensate for baseline changes, the slope threshold is decayed after a slope decay threshold number of data value samples have passed since the last edge was found. In one embodiment, the slope decay threshold is sixteen data value samples. Thus, in this embodiment, if sixteen data value samples have passed since the completion of the last edge was detected, the slope threshold is decayed 25%. Thus, in one embodiment, if the previous slope threshold (which was 9/16ths of the most recent edge slope) was 36, for example, the new slope threshold after the sixteen data value samples of not seeing an absolute value of slope exceeding the slope threshold would be 36×0.75=27.

In one embodiment, after the bit transitions have been detected, they may be determined to be high or low bits, based on whether the leading edge of a bit or string of bits is rising or falling. Further, a number of bits being represented by a particular pair of edge transitions may be determined by comparing the time between successive rising and falling edges. In one embodiment, the midpoints of successive rising and falling edges are determined, and the time period between the two midpoints are compared against the expected frequency of the received information, in order to determine how many of which kind of bit the data represents.

Further, in one or more embodiments, the bits are either stored for later analysis, or may be analyzed as enough bits come in to interpret.

FIGS. 3A, 3B, 3C and 3D together depict a process diagram showing a process for processing information in accordance with one embodiment.

Figure 3A:
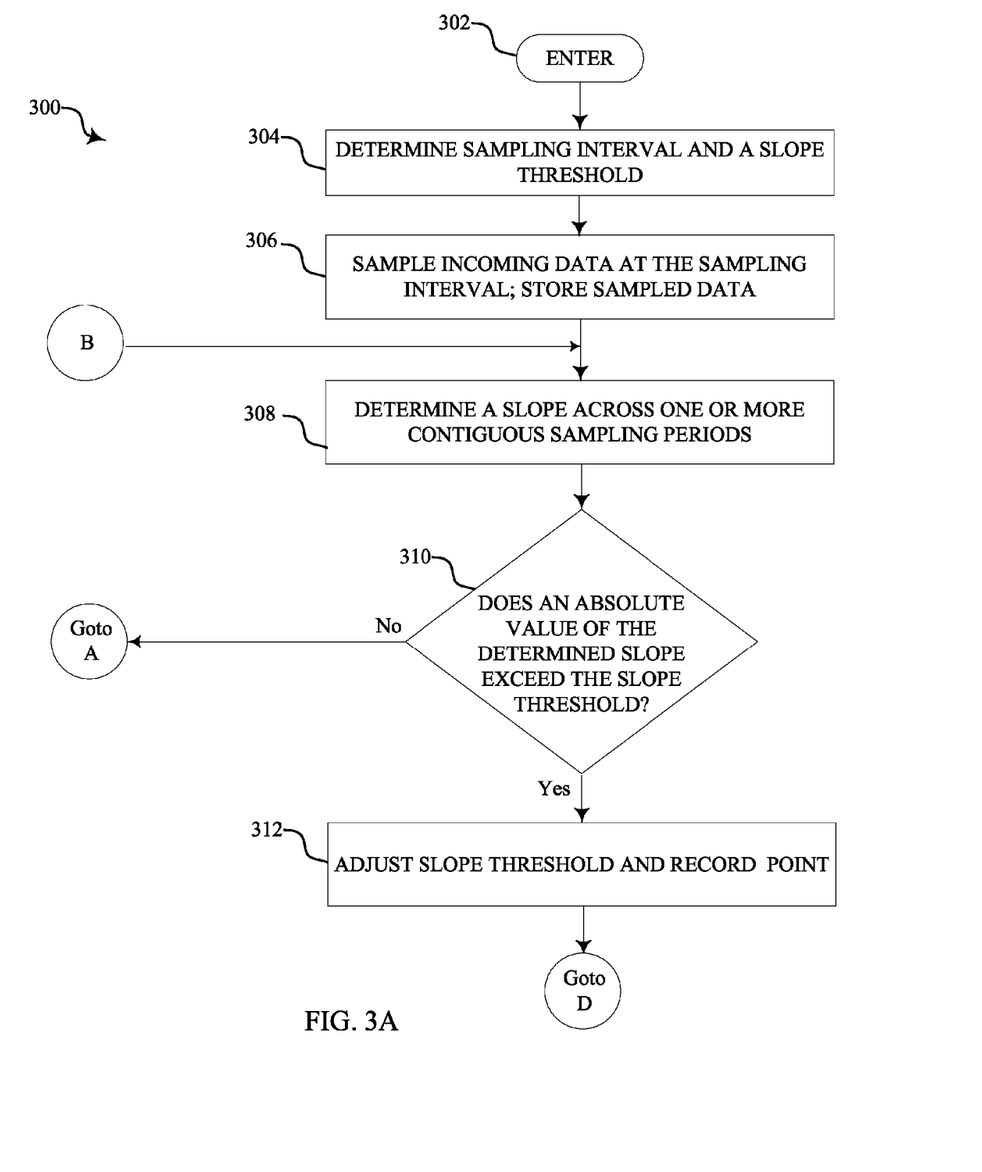
FIGS. 3A, 3B, 3C and 3D together depict a process diagram showing a process for processing information in accordance with one embodiment.

Referring to FIG. 3A, Process 300 for processing information begins at ENTER OPERATION 302 and process flow proceeds to DETERMINE SAMPLING INTERVAL AND A SLOPE THRESHOLD OPERATION 304.

At DETERMINE SAMPLING INTERVAL AND A SLOPE THRESHOLD OPERATION 304, an appropriate sampling interval is determined, at least partly based on the expected frequency of data to be sent from the first device to the second device.

In various embodiments, at DETERMINE SAMPLING INTERVAL AND A SLOPE THRESHOLD OPERATION 304, the sampling rate is a multiple of the expected frequency of the data transmission from the first device.

In one illustrative example, at DETERMINE SAMPLING INTERVAL AND A SLOPE THRESHOLD OPERATION 304, an expected data frequency might be approximately 9600 bits per second, or more or less, with a sampling rate of approximately 44,100 samples per second, or more, or less. Other data sampling rates and other expected data transmission frequencies may be used along these guidelines at DETERMINE SAMPLING INTERVAL AND A SLOPE THRESHOLD OPERATION 304, while remaining within the scope and purpose of the process for processing information disclosed herein.

As discussed above, for initial edge detection, an initial slope threshold is needed to be determined or set. In one embodiment, a slope threshold may be initially determined at DETERMINE SAMPLING INTERVAL AND A SLOPE THRESHOLD OPERATION 304 based on a noise test, where data value samples are taken while the system is not receiving any data from the first device.

In one embodiment, initial edge detection is accomplished by determining a sample event where the absolute value of the slope of the data value samples near that event are more than a multiple of the prior slopes. In that example, an initial slope threshold is determined at DETERMINE SAMPLING INTERVAL AND A SLOPE THRESHOLD OPERATION 304 to be a multiple of the absolute value of the most recent prior slope, determined when there was no data being received from the first device. Thus, on initial detection of what is believed to be data incoming from the first device, if the absolute value of the slope of a proposed initial edge is at least three times an absolute value of the slope of the data values samples preceding it, it is likely that an initial edge has been detected.

In various embodiments, prior to the beginning of data sampling, and optionally at DETERMINE SAMPLING INTERVAL AND A SLOPE THRESHOLD OPERATION 304, test samples may be obtained to determine a degree of noise activity that is statically present in Application Platform 108.

As an example, data value samples taken at DETERMINE SAMPLING INTERVAL AND A SLOPE THRESHOLD OPERATION 304 prior to any information being sent from the first device might result in six data value samples: 10, 0, 10, 5, 8, 7. In this example, following the sixth data value sample of 7, information from the first device is received at the second device, with the first "real" information resulting in a data value sample of 30. In various embodiments, an atypical noise value being received, such as a data value sample representing at least three times the value of an immediately prior data value sample, here seen in this example as an immediate prior data value sample of 7, is seen as the beginning of actual data, and is treated as such by the process for processing information as discussed herein.

Alternatively, in another illustrative example, and in one embodiment, in order to validate a particular sampling event as being part of a true initial edge, as compared with being a noise spike, an increase in slope greater than a predetermined threshold is desired, with the predetermined threshold being based, at least in part on the absolute value of the most recent prior detected slope. In one illustrative example, the desired difference in absolute value of slope at DETERMINE SAMPLING INTERVAL AND A SLOPE THRESHOLD OPERATION 304 is 20. Thus, in order to validate a slope for initial edge detection, the absolute value of a second slope would have to exceed an absolute value of an immediately prior slope by at least the threshold amount. In one embodiment, the initial edge detection slope threshold is 20. Thus, in this illustrative example, an initial edge would be considered to be detected if an absolute value of the first slope is 20 units less than the absolute value of a slope that successively follows the first.

In one embodiment, once a sampling interval and a slope threshold have been determined at DETERMINE SAMPLING INTERVAL AND A SLOPE THRESHOLD OPERATION 304 process flow proceeds to SAMPLE INCOMING DATA AT THE SAMPLING INTERVAL; STORE SAMPLED DATA 306.

At SAMPLE INCOMING DATA AT THE SAMPLING INTERVAL; STORE SAMPLED DATA OPERATION 306, incoming information being received at the second device from the first device is sampled at the sampling intervals previously determined at DETERMINE SAMPLING INTERVAL AND A SLOPE THRESHOLD OPERATION 304. Optionally, the sampled data may be stored in a storage location and operated on at an appropriate later time.

Suitable storage locations for the storage of the incoming sampled data include, but are not limited to Data 208 of Memory 204, or any other temporary or permanent data location known to persons of ordinary skill having the benefit of this disclosure.

As used herein, memory and storage refers to any volatile memory, any nonvolatile memory, or any combination of the two.

Once enough sampled data is available to determine a slope, or when all incoming information from the first device has been received, or somewhere in between, process flow proceeds to DETERMINE A SLOPE ACROSS ONE OR MORE CONTIGUOUS SAMPLING PERIODS OPERATION 308.

In various embodiments, at DETERMINE A SLOPE ACROSS ONE OR MORE CONTIGUOUS SAMPLING PERIODS OPERATION 308, and using Slope Detector 212 of Application Platform 108, an absolute value of slope of earlier incoming data values is determined prior to designating the incoming data that follows as valid, to ensure that the received data value sample represents actual data. In various embodiments, the slope is determined at DETERMINE A SLOPE ACROSS ONE OR MORE CONTIGUOUS SAMPLING PERIODS OPERATION 308, and using Slope Detector 212 of Application Platform 108, by taking an absolute value of the difference of two data values samples, divided by the number of data sampling periods over which the data value samples were obtained.

In one embodiment, at DETERMINE A SLOPE ACROSS ONE OR MORE CONTIGUOUS SAMPLING PERIODS OPERATION 308, and using Slope Detector 212 of Application Platform 108, the slope is determined by using two data value samples taken contiguous in time, with the second data sample value taken one data sample period after the first data value sample was taken. In one embodiment, an absolute value of the previously determined slope is also determined, and optionally stored if desired.

Alternatively, at DETERMINE A SLOPE ACROSS ONE OR MORE CONTIGUOUS SAMPLING PERIODS OPERATION 308, and using Slope Detector 212 of Application Platform 108, the two data value samples used in the determination of a slope may be two or more sampling periods apart.

In one illustrative example, at DETERMINE A SLOPE ACROSS ONE OR MORE CONTIGUOUS SAMPLING PERIODS OPERATION 308, and using Slope Detector 212 of Application Platform 108, in an obtained data value sample set having data value samples 10, 29, 85, two data sampling periods are involved, the first data sampling period being between the time the first data value sample of 10 was obtained and the second data value sample of 29 was obtained, and the second data sampling period being between the time the second data value sample of 29 was obtained and the third data value sample of 85 was obtained.

In one illustrative example using this data, at DETERMINE A SLOPE ACROSS ONE OR MORE CONTIGUOUS SAMPLING PERIODS OPERATION 308, and using Slope Detector 212 of Application Platform 108, in one embodiment, the first two exemplary data value samples are used to calculate a slope, the difference between the first two data value samples is obtained, resulting in 19, and that result is subsequently divided by the number of sampling periods between the two data points, e.g. one, resulting in a slope of 29 minus 10 equals 19, the absolute value of which is 19.

This particular determination of slope at DETERMINE A SLOPE ACROSS ONE OR MORE CONTIGUOUS SAMPLING PERIODS OPERATION 308 and using Slope Detector 212 of Application Platform 108 is determined using $$\text{slope} = \frac{|y_n - y_1|}{n - 1}$$

where the values of y are the later and earlier data value samples being considered, respectively, and the difference calculation in the denominator is the number of sampling periods between the values used in the numerator. Thus, at DETERMINE A SLOPE ACROSS ONE OR MORE CONTIGUOUS SAMPLING PERIODS OPERATION 308, if the data values are 10 and 29, the numerator is 19 (the second data value samples minus the first) and the denominator is 1, the number of sample periods between the two data value samples used in the numerator.

In a second illustrative example using the same data value samples from above, and in one embodiment, at DETERMINE A SLOPE ACROSS ONE OR MORE CONTIGUOUS SAMPLING PERIODS OPERATION 308, and using Slope Detector 212 of Application Platform 108, the first and third exemplary data value samples are used to calculate a slope, the difference between the two data value samples is obtained, resulting in 85 minus 10 equaling 75, and is subsequently divided by the number of sampling periods between the two data points, e.g. two, in this example, resulting in a slope of 75 divided by two equaling 37.5, the absolute value of which is 37.5.

Using the process described above, rising and falling edges may be detected. In one embodiment, for slopes that are not part of an initial edge, a slope threshold may be used to determine subsequent rising or falling edges in the data.

Regardless of which method is used to determine a slope of the data sample values, and optionally an absolute value of the slope of the data sample values, in one embodiment, the method is used on each subsequent data value sample set, and results obtained, to ensure that the current slope and absolute value of the slope of the most recently analyzed data is known.

For example, in one embodiment, if at DETERMINE A SLOPE ACROSS ONE OR MORE CONTIGUOUS SAMPLING PERIODS OPERATION 308, a first, second and third data value sample are under consideration, once the resulting slope, and optionally an absolute value of the slope, for that data set is determined, the next set may optionally consist of the second and third data value samples considered with a fourth data value sample, where the fourth data value sample was the next most recent data value sample taken after data value sample three was taken.

In one embodiment, once a slope has been determined at DETERMINE A SLOPE ACROSS ONE OR MORE CONTIGUOUS SAMPLING PERIODS OPERATION 308, process flow proceeds to DOES AN ABSOLUTE VALUE OF THE DETERMINED SLOPE EXCEED THE SLOPE THRESHOLD? OPERATION 310.

In one embodiment, at DOES AN ABSOLUTE VALUE OF THE DETERMINED SLOPE EXCEED THE SLOPE THRESHOLD? OPERATION 310, a determination is made as to whether the absolute value of the slope determined at DETERMINE A SLOPE ACROSS ONE OR MORE CONTIGUOUS SAMPLING PERIODS OPERATION 308 meets or exceeds the slope threshold set at DETERMINE SAMPLING INTERVAL AND A SLOPE THRESHOLD OPERATION 304.

In one embodiment, if the absolute value of the slope determined at DETERMINE A SLOPE ACROSS ONE OR MORE CONTIGUOUS SAMPLING PERIODS OPERATION 308 meets or exceeds the slope threshold set at DETERMINE SAMPLING INTERVAL AND A SLOPE THRESHOLD OPERATION 304, process flow proceeds to ADJUST SLOPE THRESHOLD AND RECORD POINT OPERATION 312.

Once the slope magnitude determined at DETERMINE A SLOPE ACROSS ONE OR MORE CONTIGUOUS SAMPLING PERIODS OPERATION 308 is greater than or equal to the slope threshold, the process detects that the beginning of an edge has been found.

In one embodiment, at ADJUST SLOPE THRESHOLD AND RECORD POINT OPERATION 312, the first of the two points used to determine a slope at DETERMINE A SLOPE ACROSS ONE OR MORE CONTIGUOUS SAMPLING PERIODS OPERATION 308 is recorded for later use along with an indication of the time or position of the sampling event relating to the recorded point.

In one embodiment, at ADJUST SLOPE THRESHOLD AND RECORD POINT OPERATION 312, a new slope threshold is also determined, the determination being at least partly based on the slope determined at DETERMINE A SLOPE ACROSS ONE OR MORE CONTIGUOUS SAMPLING PERIODS OPERATION 308 which met or exceeded the slope threshold set at DETERMINE SAMPLING INTERVAL AND A SLOPE THRESHOLD OPERATION 304.

In one embodiment, the new slope threshold determined at ADJUST SLOPE THRESHOLD AND RECORD POINT OPERATION 312 is a predetermined fraction of the actual slope determined at DETERMINE A SLOPE ACROSS ONE OR MORE CONTIGUOUS SAMPLING PERIODS OPERATION 308 which met or exceeded the slope threshold set at DETERMINE SAMPLING INTERVAL AND A SLOPE THRESHOLD OPERATION 304.

In one embodiment, the new slope threshold determined at ADJUST SLOPE THRESHOLD AND RECORD POINT OPERATION 312 is between one half and three quarters of the actual slope determined at DETERMINE A SLOPE ACROSS ONE OR MORE CONTIGUOUS SAMPLING PERIODS OPERATION 308 which met or exceeded the slope threshold set at DETERMINE SAMPLING INTERVAL AND A SLOPE THRESHOLD OPERATION 304.

In one embodiment, the new slope threshold determined at ADJUST SLOPE THRESHOLD AND RECORD POINT OPERATION 312 is determined by multiplying the actual slope determined at DETERMINE A SLOPE ACROSS ONE OR MORE CONTIGUOUS SAMPLING PERIODS OPERATION 308 which met or exceeded the slope threshold set at DETERMINE SAMPLING INTERVAL AND A SLOPE THRESHOLD OPERATION 304 by $9/16$.

In one embodiment, once the slope threshold has been adjusted and the first of the two points used to determine a slope recorded, at ADJUST SLOPE THRESHOLD AND RECORD POINT OPERATION 312, process flow proceeds to GET MORE DATA; DETERMINE A SLOPE ACROSS ONE OR MORE CONTIGUOUS SAMPLING PERIODS OPERATION 314.

In one embodiment, at GET MORE DATA; DETERMINE A SLOPE ACROSS ONE OR MORE CONTIGUOUS SAMPLING PERIODS OPERATION 314, additional data is obtained, either through sampling or through retrieving previously sampled data value samples from a location where previously sampled data was stored. The obtained data is data that immediately followed the point recorded at ADJUST SLOPE THRESHOLD AND RECORD POINT OPERATION 312.

In various embodiments, at GET MORE DATA; DETERMINE A SLOPE ACROSS ONE OR MORE CONTIGUOUS SAMPLING PERIODS OPERATION 314, and using Slope Detector 212 of Application Platform 108, the slope of the current data is determined by taking an absolute value of the difference of two data value samples, divided by the number of data sampling periods over which the data value samples were obtained.

In one embodiment, at GET MORE DATA; DETERMINE A SLOPE ACROSS ONE OR MORE CONTIGUOUS SAMPLING PERIODS OPERATION 314, and using Slope Detector 212 of Application Platform 108, the slope is determined by using two data value samples taken contiguous in time, with the second data sample value taken one data sample period after the first data value sample was taken.

Alternatively, at GET MORE DATA; DETERMINE A SLOPE ACROSS ONE OR MORE CONTIGUOUS SAMPLING PERIODS OPERATION 314, and using Slope Detector 212 of Application Platform 108, the two data value samples used in the determination of a slope may be two or more sampling periods apart.

In one illustrative example, at GET MORE DATA; DETERMINE A SLOPE ACROSS ONE OR MORE CONTIGUOUS SAMPLING PERIODS OPERATION 314, and using Slope Detector 212 of Application Platform 108, in an obtained data value sample set having data value samples 85, 29, 10, two data sampling periods are involved, the first data sampling period being between the time the first data sample of 85 was obtained and the second data sample value of 29 was obtained, and the second data sampling period being between the time the second data sample of 29 was obtained and the third data sample value of 10 was obtained.

In one illustrative example using this data, at GET MORE DATA; DETERMINE A SLOPE ACROSS ONE OR MORE CONTIGUOUS SAMPLING PERIODS OPERATION 314, and using Slope Detector 212 of Application Platform 108, in one embodiment, the first two exemplary data value samples are used to calculate a slope, the difference between the first two data value samples is obtained, resulting in −56, and that result is subsequently divided by the number of sampling periods between the two data points, e.g. one, resulting in a slope of 29 minus 85 equals −56.

This particular determination of slope at GET MORE DATA; DETERMINE A SLOPE ACROSS ONE OR MORE CONTIGUOUS SAMPLING PERIODS OPERATION 314 and using Slope Detector 212 of Application Platform 108 is determined using $$\text{slope} = \frac{|y_n - y_1|}{n - 1}$$

where the values of y are the later and earlier data value samples being considered, respectively, and the difference calculation in the denominator is the number of sampling periods between the values used in the numerator. Thus, at GET MORE DATA; DETERMINE A SLOPE ACROSS ONE OR MORE CONTIGUOUS SAMPLING PERIODS OPERATION 314, if the data values are 29 and 10, the numerator is negative nineteen (−19), (the second data value sample minus the first) and the denominator is 1, the number of sample periods between the two data value samples used in the numerator.

In a second illustrative example using the same data samples from above, and in one embodiment, at GET MORE DATA; DETERMINE A SLOPE ACROSS ONE OR MORE CONTIGUOUS SAMPLING PERIODS OPERATION 314, and using Slope Detector 212 of Application Platform 108, the first and third exemplary data samples are used to calculate a slope, the difference between the two data value samples is obtained, resulting in 10 minus 85 equaling negative seventy-five (−75), and is subsequently divided by the number of sampling periods between the two data points, e.g. two, in this example, resulting in a slope of [(−75) divided by two] equaling −37.5, the absolute value of which is 37.5.

Again, using the process described above, rising and falling edges may be detected. In one embodiment, for slopes that are not part of an initial edge, a slope threshold may be used to determine subsequent rising or falling edges in the data.

Regardless of which method is used to determine a slope of the data sample values, in one embodiment, the method is used on each subsequent data value sample set, and results obtained, to ensure that the current slope of the most recently analyzed data is known.

For example, in one embodiment, if at DETERMINE A SLOPE ACROSS ONE OR MORE CONTIGUOUS SAMPLING PERIODS OPERATION 308, a first, second and third data value sample are under consideration, once the resulting slope for that data set is determined, the next set may optionally consist of the second and third data value samples considered with a fourth data value sample, where the fourth data value sample was the next most recent data value sample taken after the third data value sample was taken.

Figure 3B:
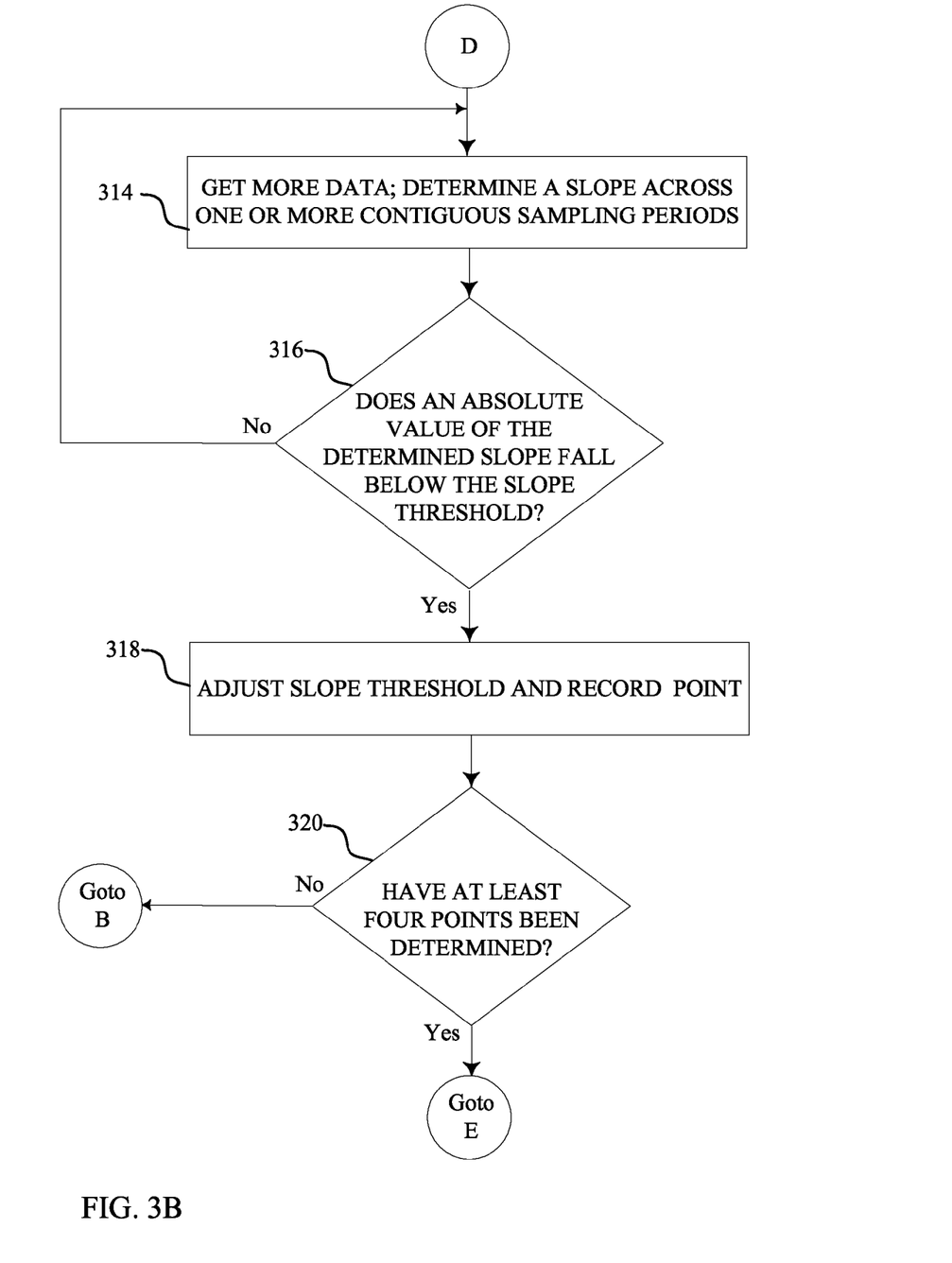

In one embodiment, once a slope has been determined at GET MORE DATA; DETERMINE A SLOPE ACROSS ONE OR MORE CONTIGUOUS SAMPLING PERIODS OPERATION 314, process flow proceeds to DOES AN ABSOLUTE VALUE OF THE DETERMINED SLOPE FALL BELOW THE SLOPE THRESHOLD? OPERATION 316.

In one embodiment, at DOES AN ABSOLUTE VALUE OF THE DETERMINED SLOPE FALL BELOW THE SLOPE THRESHOLD? OPERATION 316, a determination is made as to whether the slope determined at GET MORE DATA; DETERMINE A SLOPE ACROSS ONE OR MORE CONTIGUOUS SAMPLING PERIODS OPERATION 314 falls below the slope threshold set at ADJUST SLOPE THRESHOLD AND RECORD POINT OPERATION 312.

In one embodiment, if the slope determined at GET MORE DATA; DETERMINE A SLOPE ACROSS ONE OR MORE CONTIGUOUS SAMPLING PERIODS OPERATION 314 falls below the slope threshold set at ADJUST SLOPE THRESHOLD AND RECORD POINT OPERATION 312, process flow proceeds to ADJUST SLOPE THRESHOLD AND RECORD POINT OPERATION 318.

Once the slope determined at GET MORE DATA; DETERMINE A SLOPE ACROSS ONE OR MORE CONTIGUOUS SAMPLING PERIODS OPERATION 314 is below the slope threshold, the process detects that the flat portion following an edge has been found.

In one embodiment, at ADJUST SLOPE THRESHOLD AND RECORD POINT OPERATION 318, an appropriate one of the data value samples used to determine a slope at GET MORE DATA; DETERMINE A SLOPE ACROSS ONE OR MORE CONTIGUOUS SAMPLING PERIODS OPERATION 314 is recorded for later use, along with an indication of the time or position of the sampling event relating to the recorded data sample value.

In one embodiment, at ADJUST SLOPE THRESHOLD AND RECORD POINT OPERATION 318, a new slope threshold is also determined, the determination being at least partly based on the slope determined at GET MORE DATA; DETERMINE A SLOPE ACROSS ONE OR MORE CONTIGUOUS SAMPLING PERIODS OPERATION 314.

In one embodiment, the new slope threshold determined at ADJUST SLOPE THRESHOLD AND RECORD POINT OPERATION 318 is a predetermined fraction of the actual slope determined at GET MORE DATA; DETERMINE A SLOPE ACROSS ONE OR MORE CONTIGUOUS SAMPLING PERIODS OPERATION 314.

In one embodiment, the new slope threshold determined at ADJUST SLOPE THRESHOLD AND RECORD POINT OPERATION 318 is between one half and three quarters of the actual slope determined at GET MORE DATA; DETERMINE A SLOPE ACROSS ONE OR MORE CONTIGUOUS SAMPLING PERIODS OPERATION 314.

In one embodiment, the new slope threshold determined at ADJUST SLOPE THRESHOLD AND RECORD POINT OPERATION 318 is determined by multiplying the actual slope determined at GET MORE DATA; DETERMINE A SLOPE ACROSS ONE OR MORE CONTIGUOUS SAMPLING PERIODS OPERATION 314 by 9/16.

In one embodiment, once a new slope threshold has been determined at ADJUST SLOPE THRESHOLD AND RECORD POINT OPERATION 318, process flow proceeds to HAVE AT LEAST FOUR POINTS BEEN DETERMINED? OPERATION 320.

At HAVE AT LEAST FOUR POINTS BEEN DETERMINED? OPERATION 320, a determination is made as to whether four points have been determined in this cycle. If only two have been determined so far, we are at the flat top or flat bottom of a bit transition, and we thus have not completed the full transition, and thus cannot yet analyze any data from this cycle.

If at HAVE AT LEAST FOUR POINTS BEEN DETERMINED? OPERATION 320 it is determined that four points have been determined and saved in memory or stored, process flow proceeds with DETERMINE HOW MANY SAMPLING PERIODS HAVE PASSED BETWEEN THE FIRST POINT AND THE FOURTH POINT OPERATION 322.

In one embodiment, at DETERMINE HOW MANY SAMPLING PERIODS HAVE PASSED BETWEEN THE FIRST POINT AND THE FOURTH POINT OPERATION 322, a determination is made as to how many sampling periods have passed between the first point and the fourth point. In one embodiment, at DETERMINE HOW MANY SAMPLING PERIODS HAVE PASSED BETWEEN THE FIRST POINT AND THE FOURTH POINT OPERATION 322 a determination is made as to how much time has passed between a time when the first point was sampled and when the fourth point was sampled. Recall that a time or sampling position was stored with each point as they were determined. In one embodiment, that time, if stored, or the position may be used together with the same data for other points to decide how many sampling periods each high or low bit transition lasted.

Following a determination of how many sampling periods have passed between the first point and the fourth point at DETERMINE HOW MANY SAMPLING PERIODS HAVE PASSED BETWEEN THE FIRST POINT AND THE FOURTH POINT OPERATION 322, process flow proceeds to COMPARE TO EXPECTED FREQUENCY OF INCOMING DATA TO DETERMINE THE NUMBER OF BITS OF INFORMATION OPERATION 324.

In one embodiment, at COMPARE TO EXPECTED FREQUENCY OF INCOMING DATA TO DETERMINE THE NUMBER OF BITS OF INFORMATION OPERATION 324, comparing the time between the first point and the fourth point determined at DETERMINE HOW MANY SAMPLING PERIODS HAVE PASSED BETWEEN THE FIRST POINT AND THE FOURTH POINT OPERATION 322, together with the expected frequency of the received data, a determination may be made as to how many bits are included in the constant level since the previous bit transition up to the bit transition being analyzed.

In one embodiment, an alternate way of determining how many bits were represented in a given bit transition period may be accomplished using the midpoint of the rising edge line and the midpoint of the falling edge line.

In one embodiment, edge center points may be found by finding the largest magnitude slope between the edge start point and the edge end point and subtracting ([samples per slope]−1)/2. For example, in one illustrative example where the number of samples being used to compute each slope is 3, then the time coordinate of the edge center point is the coordinate of the largest magnitude slope minus [(3−1)/2]=2/2=1.

This is also formulated as $$\text{edge midpoint} = x \text{ coordinate} - \frac{(\text{samples per slope} - 1)}{2},$$

where the x coordinate terminates the segment with the largest slope.

Figure 3C:
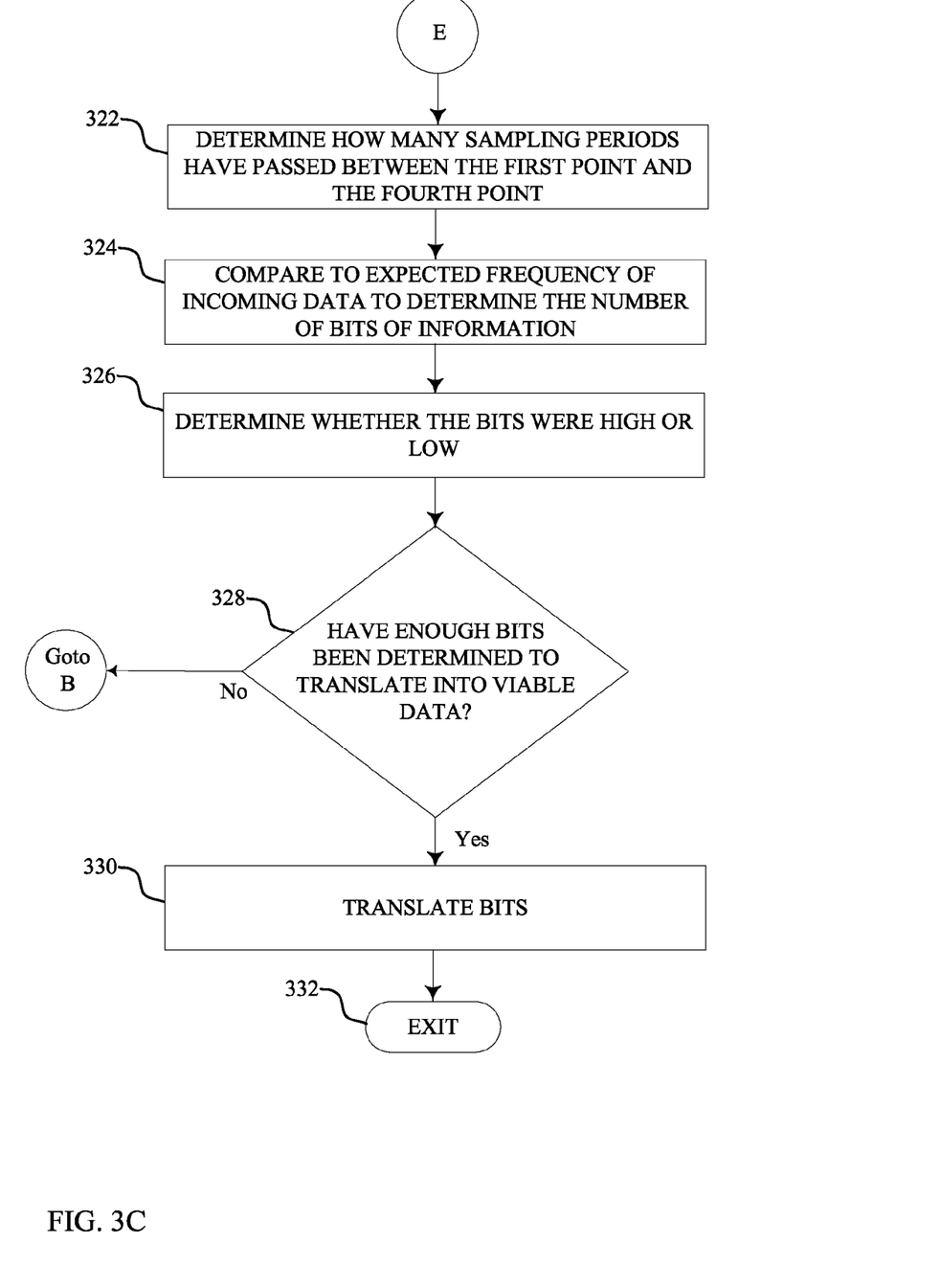

Following the determination of how many bits were involved in the most recently analyzed bit transition at COMPARE TO EXPECTED FREQUENCY OF INCOMING DATA TO DETERMINE THE NUMBER OF BITS OF INFORMATION OPERATION 324, process flow proceeds to DETERMINE WHETHER THE BITS WERE HIGH OR LOW OPERATION 326.

In one embodiment, at DETERMINE WHETHER THE BITS WERE HIGH OR LOW OPERATION 326, a determination is made as to whether the number of bits determined at COMPARE TO EXPECTED FREQUENCY OF INCOMING DATA TO DETERMINE THE NUMBER OF BITS OF INFORMATION OPERATION 324 are high bits or are alternatively low bits.

In one embodiment, the slope transition at or near the first point is examined to determine whether the slope following the first point is positive, which would indicate that the number of bits determined at COMPARE TO EXPECTED FREQUENCY OF INCOMING DATA TO DETERMINE THE NUMBER OF BITS OF INFORMATION OPERATION 324 are high bits representing a binary high.

In one embodiment, at DETERMINE WHETHER THE BITS WERE HIGH OR LOW OPERATION 326, the slope transition at the first point is examined to determine whether the slope following the first point is negative, which would indicate that the number of bits determined at COMPARE TO EXPECTED FREQUENCY OF INCOMING DATA TO DETERMINE THE NUMBER OF BITS OF INFORMATION OPERATION 324 are low bits representing a binary low.

In one embodiment, at DETERMINE WHETHER THE BITS WERE HIGH OR LOW OPERATION 326, the slope transition at or near the third point is examined to determine whether the slope following the third point is negative, which would indicate that the number of bits determined at COMPARE TO EXPECTED FREQUENCY OF INCOMING DATA TO DETERMINE THE NUMBER OF BITS OF INFORMATION OPERATION 324 are high bits representing a binary high.

In one embodiment, the slope transition at the third point is examined to determine whether the slope following the third point is positive, which would indicate that the number of bits determined at COMPARE TO EXPECTED FREQUENCY OF INCOMING DATA TO DETERMINE THE NUMBER OF BITS OF INFORMATION OPERATION 324 are low bits representing a binary low.

Following the determination of whether the bits were high or low at DETERMINE WHETHER THE BITS WERE HIGH OR LOW OPERATION 326, process flow proceeds to HAVE ENOUGH BITS BEEN DETERMINED TO TRANSLATE INTO VIABLE DATA? OPERATION 328.

In one embodiment, at HAVE ENOUGH BITS BEEN DETERMINED TO TRANSLATE INTO VIABLE DATA? OPERATION 328, a determination is made as to whether enough bits have been detected to be able to translate those bits into a form of information or commands usable to Application 216 or Application Platform 108.

In one embodiment, bits are transmitted in single bytes, each byte being an 8-bit group of bits, optionally with one or more parity bits included.

In one embodiment, a single byte is enough to translate into data or commands useful to Application 216 or Application Platform 108.

In one embodiment, two or more bytes are needed in order to translate the processed bits into data or commands useful to Application 216 and/or Application Platform 108.

If at HAVE ENOUGH BITS BEEN DETERMINED TO TRANSLATE INTO VIABLE DATA? OPERATION 328 enough bits have been processed to translate the processed bits into data or commands useful to Application 216 and/or Application Platform 108, process flow proceeds to TRANSLATE BITS OPERATION 330 where the bits are translated.

Following the translation of bits at TRANSLATE BITS OPERATION 330, process flow ends at EXIT OPERATION 332.

Figure 3D:
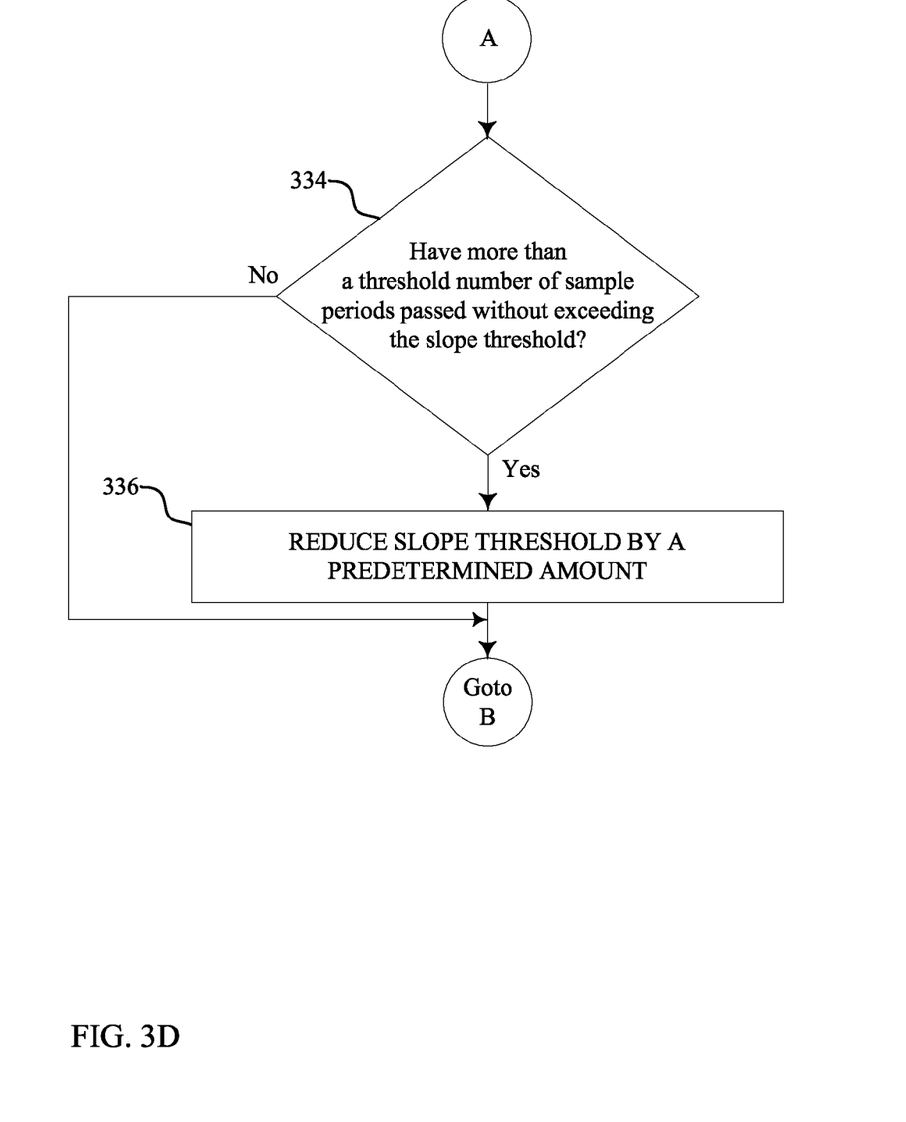

If at DOES AN ABSOLUTE VALUE OF THE DETERMINED SLOPE EXCEED THE SLOPE THRESHOLD? OPERATION 310, a determination is made that an absolute value of the determined slope does not exceed the slope threshold, process flow proceeds with HAVE MORE THAN A THRESHOLD NUMBER OF SAMPLE PERIODS PASSED WITHOUT EXCEEDING THE SLOPE THRESHOLD? OPERATION 334.

Due to variations within a receiving device, baselines may change significantly over a long period of time involving many data sampling periods. In order to compensate for baseline changes, the slope threshold is decayed after a slope decay threshold number of data points since the last edge was found.

At HAVE MORE THAN A THRESHOLD NUMBER OF SAMPLE PERIODS PASSED WITHOUT EXCEEDING THE SLOPE THRESHOLD? OPERATION 334, it is determined whether a slope decay threshold number of sampling periods have passed since the last point was recorded, or alternatively when the last time the slope failed to exceed the slope threshold. In one embodiment, the slope decay threshold is ten or greater than ten. In one embodiment, the slope decay threshold is sixteen.

Thus, in an illustrative example, and in one embodiment where the slope decay threshold is sixteen, if sixteen data value samples have passed without an edge being detected, the slope threshold process flow proceeds to REDUCE SLOPE THRESHOLD BY A PREDETERMINED AMOUNT OPERATION 336 where the current slope threshold is decayed by a predetermined amount.

In one embodiment, at REDUCE SLOPE THRESHOLD BY A PREDETERMINED AMOUNT WHERE THE CURRENT SLOPE THRESHOLD OPERATION 336 the current slope threshold is decayed by an amount greater than ten percent of the value of the current slope threshold.

In one embodiment, at REDUCE SLOPE THRESHOLD BY A PREDETERMINED AMOUNT WHERE THE CURRENT SLOPE THRESHOLD OPERATION 336 the current slope threshold is decayed by twenty-five percent of the value of the current slope threshold.

Thus, using the 25% decay as an illustrative example, if at REDUCE SLOPE THRESHOLD BY A PREDETERMINED AMOUNT WHERE THE CURRENT SLOPE THRESHOLD OPERATION 336 the current slope threshold (which was 9/16ths of the most recent edge slope) was 36, for example, the new slope threshold after the sixteen data value samples of not seeing an absolute value of slope exceeding the slope threshold would be 36×0.75=27.

Following a slope threshold reduction at REDUCE SLOPE THRESHOLD BY A PREDETERMINED AMOUNT WHERE THE CURRENT SLOPE THRESHOLD OPERATION 336, process flow proceeds at DETERMINE A SLOPE ACROSS ONE OR MORE CONTIGUOUS SAMPLING PERIODS OPERATION 308.

If, at HAVE MORE THAN A THRESHOLD NUMBER OF SAMPLE PERIODS PASSED WITHOUT EXCEEDING THE SLOPE THRESHOLD 334, a determination is made that a threshold number of sample periods have not passed without an edge being seen, process flow proceeds at DETERMINE A SLOPE ACROSS ONE OR MORE CONTIGUOUS SAMPLING PERIODS OPERATION 308.

If, at DOES AN ABSOLUTE VALUE OF THE DETERMINED SLOPE FALL BELOW THE SLOPE THRESHOLD? OPERATION 316, a determination is made that the slope determined at GET MORE DATA; DETERMINE A SLOPE ACROSS ONE OR MORE CONTIGUOUS SAMPLING PERIODS OPERATION 314 does not fall below the slope threshold set at ADJUST SLOPE THRESHOLD AND RECORD POINT OPERATION 312, the current slope may optionally be stored, if desired, after which process flow proceeds at GET MORE DATA; DETERMINE A SLOPE ACROSS ONE OR MORE CONTIGUOUS SAMPLING PERIODS OPERATION 314.

If, at HAVE AT LEAST FOUR POINTS BEEN DETERMINED? OPERATION 320, a determination is made that four points have not yet been determined in this cycle, process flow proceeds at DETERMINE A SLOPE ACROSS ONE OR MORE CONTIGUOUS SAMPLING PERIODS OPERATION 308.

If, at HAVE ENOUGH BITS BEEN DETERMINED TO TRANSLATE INTO VIABLE DATA? OPERATION 328, a determination is made that not enough bits have been processed to translate the processed bits into data or commands useful to Application 216 and/or Application Platform 108, process flow proceeds at DETERMINE A SLOPE ACROSS ONE OR MORE CONTIGUOUS SAMPLING PERIODS OPERATION 308.

In one embodiment, there may be periodic level transitions in the data value samples received by the second device to synchronize bit center points with the first device. Various methods may be employed by the first device to insert periodic level transitions into the data stream including, but not limited to, start bits, stop bits, and HLDC encoding.

In one embodiment, a process for processing information is a computing application or process and may be stored, in full, or in part on a computer program product. Herein, a computer program product comprises a medium and/or I/O device configured to store or transport computing system readable code, whether available or known at the time of filing or as later developed. Some examples of computer program products are CD's, DVD's, ROM cards, floppy discs, magnetic tapes, computer hard drives, portable hard drives, flash memory, volatile and non-volatile memory sticks, servers and databases on a network, or other media or process capable of delivering computer readable data representing computer readable code, whether available or known at the time of filing or as later developed. This medium may belong to a computing system. However, in some embodiments, the medium also may be removable and/or remote from the computing system.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

Using the method and system for processing information presented herein, less stable system components receiving information are accommodated, and the resulting data is much more accurate than with prior art systems.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining", "specifying", "identifying", "determining", "calculating", "using", "aggregating", "analyzing", "defining", "storing", "saving", "displaying", "categorizing", "providing", "processing", "accessing", "generating" etc., refer to the action and processes of a computing system or similar electronic device that manipulates and operates on data represented as physical (electronic) quantities within the computing system memories, resistors, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the drawing figures for method and apparatus and/or process or application for processing information discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A method for transforming data comprising:
receiving electronic information at a second device from a first device, the electronic information comprising a plurality of numerical data value samples representing successive periodic samples taken of an incoming signal, the sampling performed at sampling intervals, each sampling interval separated by sampling periods;
analyzing the data value samples, by the second device, to determine a first point, the first point being an earliest sampling point at which an absolute value of a first rate of change of data value samples reflected over one or more successive sampling periods first exceeds a predetermined slope threshold;
analyzing the data value samples, by the second device, to determine a second point taken later in time than the first point, the second point being an earliest sampling point at which an absolute value of a second rate of change of the data value samples reflected over one or more successive sampling periods is first below the predetermined slope threshold;
analyzing the data value samples, by the second device, to determine a third point taken later in time than the second point, the third point being an earliest sampling point at which an absolute value of a third rate of change of data value samples reflected over one or more successive sampling periods first exceeds the predetermined slope threshold;
analyzing, by the second device, the data value samples to determine a fourth point taken later in time than the third point, the fourth point being an earliest point at which an absolute value of a rate of change of data value samples reflected over one or more successive sampling periods falls below the predetermined slope threshold;

determining, by the second device, a number of bits of information that have been detected between the first and fourth points.

2. The method for transforming data of claim 1 further wherein determining, by the second device, a number of bits of information that have been detected between the first and fourth points comprises determining, by the second device, a number of sampling periods that have occurred between a first location and a second location, the first location being a location having a largest magnitude slope of all data value samples between the first and second points and the second location being a location having a largest magnitude slope of all data value samples between the third and fourth points.

3. The method for transforming data of claim 1 further comprising:

determining, by the second device, a number of bits of information that have been detected between the first and fourth points further comprises determining that the bits of information that have been detected are high bits representing a binary high.

4. The method for transforming data of claim 3 further wherein determining that the number of bits of information that have been detected are high bits representing a binary high comprises determining that the first rate of change is positive.

5. The method for transforming data of claim 1 further comprising:

determining that a number of bits of information that have been detected between the first and fourth points further comprises determining that the number of bits of information that have been detected are low bits representing a binary low.

6. The method for transforming data of claim 5 further wherein determining that the number of bits of information that have been detected are low bits representing a binary low comprises determining that the first rate of change in data value samples is negative.

7. The method for transforming data of claim 1 further wherein analyzing the data value samples, by the second device, to determine a first point at which an absolute value of a first rate of change of data value samples reflected over one or more successive sampling periods first exceeds a predetermined slope threshold comprises analyzing the data value samples, by the second device, to determine a first point at which an absolute value of a first rate of change of data value samples reflected over two successive sampling periods first exceeds a predetermined slope threshold.

8. The method for receiving and analyzing data of claim 1 further wherein analyzing the data value samples to determine a second point taken later in time than the first point, the second point being an earliest point at which an absolute value of a second rate of change of data value samples reflected over one or more successive sampling periods is first below the predetermined slope threshold comprises analyzing the data value samples to determine a second point taken later in time than the first point, the second point being a point at which an absolute value of a second rate of change of data value samples reflected over two successive sampling periods is first below the predetermined slope threshold.

9. The method for receiving and analyzing data of claim 1 further wherein analyzing the data value samples data samples to determine a third point taken later in time than the second point, the third point being a point at which an absolute value of a third rate of change of data value samples reflected over one or more successive sampling periods first exceeds the predetermined slope threshold comprises analyzing the data value samples to determine a third point taken later in time than the second point, the third point being a point at which an absolute value of a third rate of change of data value samples reflected over two successive sampling periods first exceeds the predetermined slope threshold.

10. The method for receiving and analyzing data of claim 1 further wherein analyzing the data value samples data samples to determine a fourth point taken later in time than the third point, the fourth point being a point at which an absolute value of a fourth rate of change of data value samples reflected over one or more successive sampling periods falls below the predetermined slope threshold comprises analyzing the data value samples to determine a fourth point taken later in time than the third point, the fourth point being a point at which an absolute value of a fourth rate of change of data value samples reflected over two successive sampling periods falls below the predetermined slope threshold.

11. The method for receiving and analyzing data of claim 1 further wherein determining a number of bits of information that have been detected between the first and fourth points comprises determining a number of sampling periods between the first point and the third point and comparing a time represented by the determined number of sampling periods to an expected frequency of the received electronic information.

12. The method for receiving and analyzing data of claim 1 further wherein determining a number of bits of information that have been detected between the first and fourth points comprises determining a number of sampling periods between the second point and the fourth point and comparing a time represented by the determined number of sampling periods to an expected frequency of the received electronic information.

13. The method for receiving and analyzing data of claim 1 further comprising:

determining that a number of sampling periods following the determination of the second point and prior to determining the third point exceeds a predetermined slope degradation threshold;

reducing the slope threshold by a previously determined amount.

14. The method for receiving and analyzing data of claim 13 further wherein determining that a number of sampling periods following the determination of the second point exceeds a predetermined slope degradation threshold comprises determining that a number of sampling periods following the determination of the second point exceeds fifteen periods; and reducing the slope threshold by a previously determined amount comprises reducing the slope threshold by twenty-five percent.

15. A system for transforming data comprising:
one or more computing processors; and
one or more memories coupled to the one or more computing processors, the one or more memories having stored therein instructions which when executed by the one or more computing processors perform a process comprising:
receiving electronic information from a first device, the electronic information comprising a plurality of numerical data value samples representing successive periodic samples taken of an incoming signal, the sampling performed at sampling intervals each sampling interval separated by sampling periods;
analyzing the data value samples to determine a first point, the first point being an earliest sampling point at which an absolute value of a first rate of change of data value samples reflected over one or more successive sampling periods first exceeds a predetermined slope threshold;
analyzing the data value samples to determine a second point taken later in time than the first point, the second point being an earliest sampling point at which an absolute value of a second rate of change of the data value samples reflected over one or more successive sampling periods is first below the predetermined slope threshold;
analyzing the data value samples to determine a third point taken later in time than the second point, the third point being an earliest sampling point at which an absolute value of a third rate of change of data value samples reflected over one or more successive sampling periods first exceeds the predetermined slope threshold;
analyzing the data value samples to determine a fourth point taken later in time than the third point, the fourth point being an earliest point at which an absolute value of a rate of change of data value samples reflected over one or more successive sampling periods falls below the predetermined slope threshold;
determining a number of bits of information that have been detected between the first and fourth points.

16. The system for transforming data of claim 15 further wherein
determining a number of bits of information that have been detected between the first and fourth points comprises determining, by the second device, a number of sampling periods that have occurred between a first location and a second location, the first location being a location having a largest magnitude slope of all data value samples between the first and second points and the second location being a location having a largest magnitude slope of all data value samples between the third and fourth points.

17. The system for transforming data of claim 16 further comprising:
determining a number of bits of information that have been detected between the first and fourth points further comprises determining that the bits of information that have been detected are high bits representing a binary high.

18. The system for transforming data of claim 17 further wherein
determining that the number of bits of information that have been detected are high bits representing a binary high comprises determining that the first rate of change is positive.

19. The system for transforming data of claim 16 further comprising:
determining that a number of bits of information that have been detected between the first and fourth points further comprises determining that the number of bits of information that have been detected are low bits representing a binary low.

20. The system for transforming data of claim 19 further wherein
determining that the number of bits of information that have been detected are low bits representing a binary low comprises determining that the first rate of change in data value samples is negative.

* * * * *